United States Patent [19]
Biard

[11] Patent Number: 5,589,935
[45] Date of Patent: Dec. 31, 1996

[54] TURBIDITY SENSOR WITH THE CAPABILITY OF REGULATING THE INTENSITY OF A LIGHT SOURCE

[75] Inventor: James R. Biard, Richardson, Tex.

[73] Assignee: Honeywell, Inc., Minneapolis, Minn.

[21] Appl. No.: 452,607

[22] Filed: May 25, 1995

[51] Int. Cl.$^6$ .......................... G01N 21/00; D06F 33/00; B08B 3/00
[52] U.S. Cl. ................ 356/339; 356/442; 68/12.02; 68/12.27; 134/113; 134/57 D
[58] Field of Search ........................ 356/441–442, 356/439, 338–339, 341, 394; 68/12.02, 12.27; 134/113, 57 D

[56] References Cited

U.S. PATENT DOCUMENTS

| | | | |
|---|---|---|---|
| 3,561,875 | 2/1971 | Ried, Jr. et al. | 356/442 |
| 3,736,431 | 5/1973 | Childs | 356/442 |
| 4,003,661 | 1/1977 | Yamano | 356/442 |
| 4,257,708 | 3/1981 | Fukuda | 356/442 |
| 4,697,925 | 10/1987 | Hyodo et al. | 356/442 |
| 5,172,572 | 12/1992 | Ono | 68/12.02 |
| 5,291,626 | 3/1994 | Molnar et al. | 356/339 |
| 5,444,531 | 8/1995 | Foreman et al. | 356/339 |
| 5,446,531 | 8/1995 | Boyer et al. | 356/339 |

Primary Examiner—Georgia Y. Epps
Assistant Examiner—Jason D. Eisenberg
Attorney, Agent, or Firm—William D. Lanyi

[57] ABSTRACT

A turbidity sensor is provided with two light sensitive components or elements. One light sensitive component is displaced from a light source, such as a light emitting diode, so that a fluid can pass therebetween. A second light sensitive component is disposed within a common compartment with the light source so that it can measure the intensity of light provided by the light source. The light source and the second light sensitive components can be individual elements, or chips, within a common component package. A regulator is provided to control the magnitude of current provided to the light source so that its light intensity can be regulated. In this manner, the intensity of light emitted by the light source, such as a light emitting diode, can be controlled regardless of the aging of the LED, the variability of LED characteristics and the temperature surrounding the LED. The constant light emission from the light source permits the other light sensitive component to be used as a reliable indication of the turbidity of a solution passing between the light source and the first light sensitive component.

4 Claims, 8 Drawing Sheets

TURBIDITY SENSOR WITH THE CAPABILITY OF REGULATING THE INTENSITY OF A LIGHT SOURCE

BACKGROUND OF THE INVENTION

1. Field of the Invention

The present invention is generally related to turbidity sensors and, more particularly, to a turbidity sensor that is provided with a means for controlling the intensity of a light source for the purpose of compensating for variability of light emitting characteristics of the light source.

2. Description of the Prior Art

Turbidity sensors are used in many different types of applications. Some turbidity sensors are used in association with machines for washing articles, such as dishwashers and washing machines. Most turbidity sensors measure the effect on a light beam by particulate matter suspended within a fluid. Some turbidity sensors use only a transmitted light signal while others use both scattered and transmitted light signals.

U.S. Pat. No. 4,257,708, which issued to Fukuda on Mar. 24, 1981, discloses an apparatus for measuring the degree of rinsing in a washing machine. It is provided with a source of light, a first phototransistor disposed to receive light emitted by the light source for producing a reference signal a second phototransistor disposed to receive the light from the light source for producing a measuring signal corresponding to the amount of light received and a calculating circuit for arithmetically operating the reference signal and the measuring signal for producing an output signal corresponding to the relative values of the reference signal and the measuring signal. A first optical path between the light source and the first phototransistor and a second optical path between the light source and the second phototransistor are both disposed in rinsing water and the length of the first optical path is set to be longer than a length of the second optical path.

U.S. Pat. No. 5,291,626, which issued to Molnar et al on Mar. 8, 1994, describes a machine for cleansing articles, such as a dishwasher, that incorporates a device for measuring the turbidity of an at least partially transparent liquid. The device includes a sensor for detecting scattered electromagnetic radiation, regardless of polarization, and a sensor for detecting transmitted electromagnetic radiation, regardless of polarization.

U.S. Pat. No. 5,172,572, which issued to Ono on Dec. 22, 1992, discloses an automatic washing apparatus for washing dirty items in a washing tank to which washing liquid is supplied. The automatic washing apparatus comprises a light emitting element for emitting light to the washing liquid which is passed through the washing tank. It also comprises a first light receiving element for receiving a linear light beam which travels through the washing liquid along the optical axes of the light emitting element, and a second light receiving element for receiving scattered light which travels through the washing liquid in directions deviated from the optical axis of the light emitting element, wherein washing conditions are controlled in accordance with the quantity of light received by the first light receiving element and the quantity of light received by the second light receiving element.

One problem that can be encountered in the operation of a turbidity sensor is the variability of the light intensity provided by a light source. If a light emitting diode is used as the light source, several factors can disadvantageously affect the intensity of light provided by the diode. For example, changes in temperature will affect the light emitted from a light emitting diode for a particular current flowing through the diode. In addition, the intensity of light from a light emitting diode decreases as the diode ages. In addition to these problems, the uniformity of the light emitting characteristics of diodes vary greatly and no two diodes from a particular batch can be assumed to be identical in their light emitting characteristic. Since most turbidity sensors operate as a function of the intensity of light received by one or more light sensitive components, it is important that the intensity of light emitted by the light source be either constant or known. It would therefore be significantly beneficial if a means were provided to assure the constancy of the light intensity from a light source in a turbidity sensor.

SUMMARY OF THE INVENTION

A turbidity sensor made in accordance with the present invention comprises a light source and a first light sensitive component. The light source and the first light sensitive component are spaced apart to provide a gap therebetween in which a fluid can be disposed. The turbidity of the fluid flowing between the first light sensitive component and the light source affects the intensity of light received by the light sensitive component. In addition, a preferred embodiment of the present invention comprises a means for regulating the intensity of light emanating from the light source to a predetermined magnitude. The regulating means can comprise a second light sensitive component and a means for comparing a first signal from the second light sensitive component to a threshold magnitude. In addition, the turbidity sensor comprises a means for providing a second signal which is representative of the difference between the first signal and the threshold magnitude.

In a particularly preferred embodiment of the present invention, the turbidity sensor further comprises a means for controlling an electrical current that is provided to the light source as a function of the second signal. The controlling means can comprise a transistor. A particularly preferred embodiment of the present invention is used in conjunction with a machine for washing articles, wherein the turbidity sensor is disposed within a water reservoir of the machine. The machine can be either a dishwasher or a washing machine used for cleansing clothes.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Figure 1:
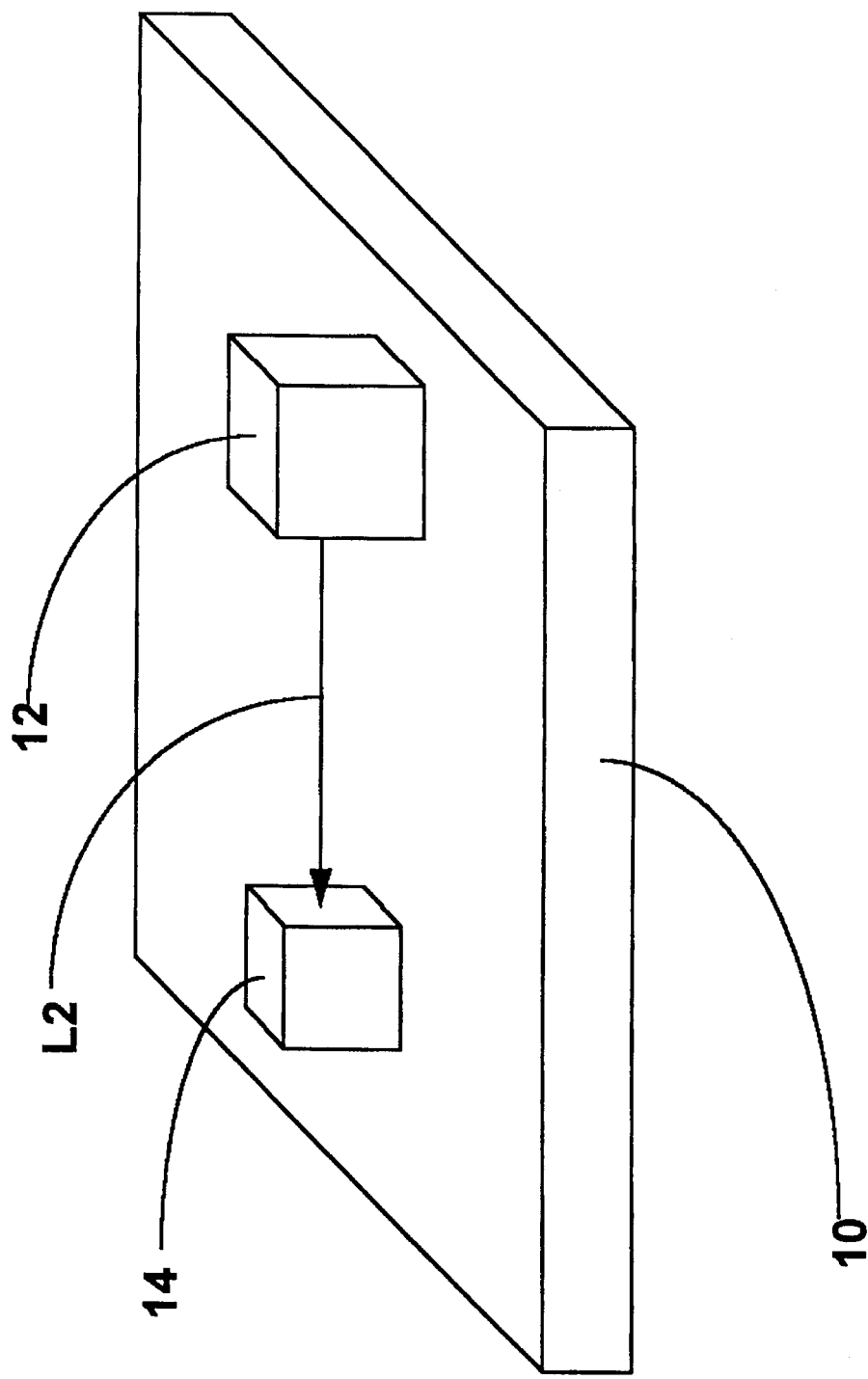
FIG. 1 illustrates a perspective schematic view of a turbidity sensor.

Throughout the Description of the Preferred Embodiment, like components will be identified by like reference numerals.

FIG. 1 shows an exemplary representation of one type of turbidity sensor. A turbidity sensor of this general type is described in U.S. patent application Ser. No. 08/246,902 (M10-15682) which was filed on May 20, 1994 and assigned to the assignee of the present application. The turbidity sensor in FIG. 1 comprises a platform 10 on which two compartments, 12 and 14, are disposed. In the first compartment 12, a light source is provided which transmits light, in the direction of arrow L2, toward a second compartment 14 in which a light sensitive component is disposed. The turbidity sensor shown in FIG. 1 can be placed within a water reservoir of a machine for washing articles so that water can flow into the region between the first and second compartments, 12 and 14. The turbidity of the water will affect the amount of light that is received by the light sensitive component within the second component 14. Although many different types of turbidity sensors can be used in combination with the present invention, the concepts of the present invention will be described in terms of their applicability to a sensor such as that illustrated in FIG. 1.

Figure 2:
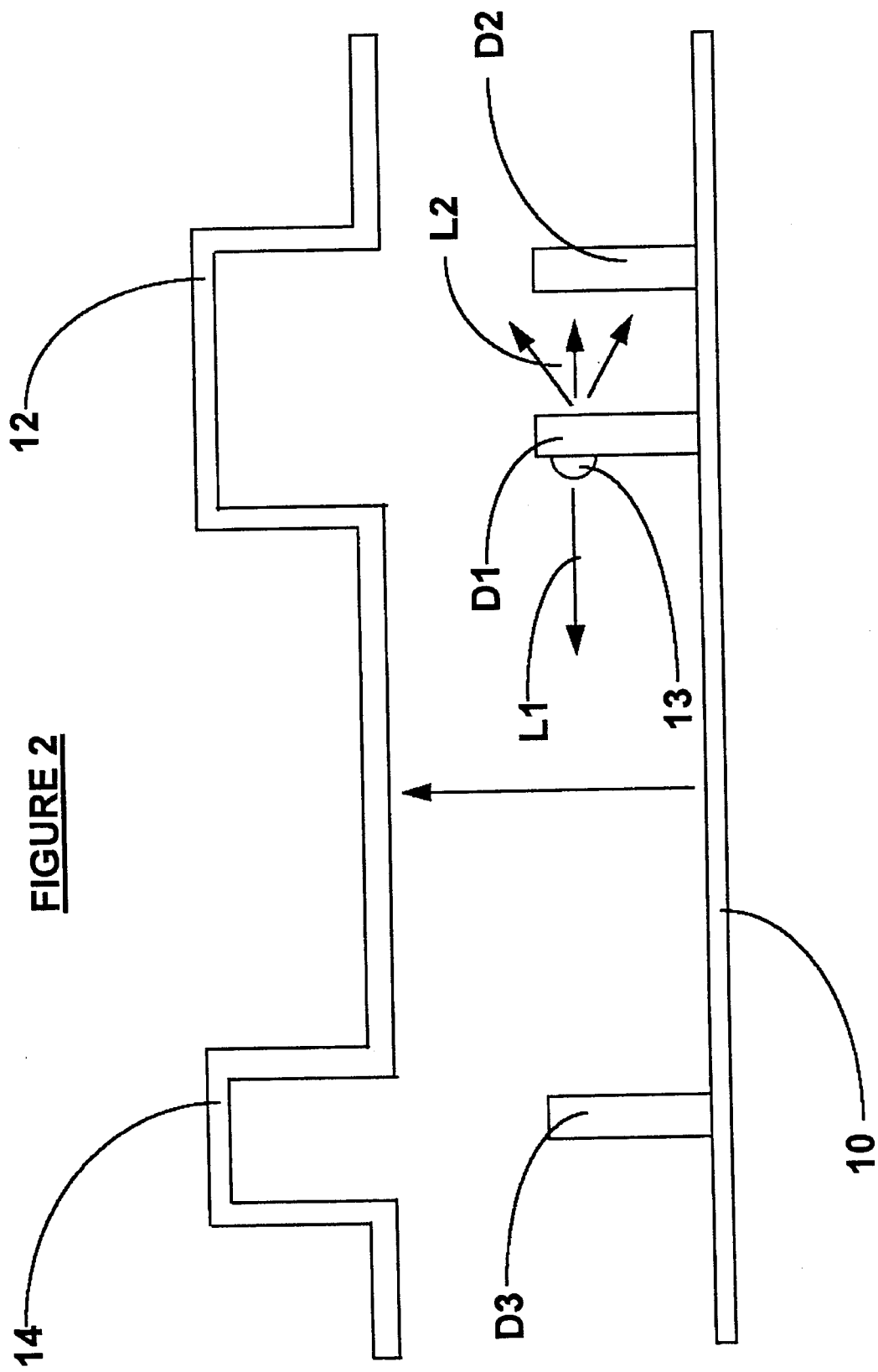
FIG. 2 illustrates an exploded view of a housing structure and a platform on which a light emitting diode and two photodiodes are attached.

FIG. 2 is an exploded view of a turbidity sensor made in accordance with the present invention. The first compartment 12 and second compartment 14 are formed as part of a plastic housing structure. The platform 10 is used to support a light source D1 and a first light sensitive component D3. In addition, a second light sensitive component D2 is attached to the platform 10. Although not illustrated in FIG. 2, it should be understood that the light source D1 and the second light sensitive component D2 are connected together in electrical communication as will be described in greater detail below. The housing structure is shaped to receive the components attached to the platform 10 when the platform 10 is inserted in the direction represented by the arrow in FIG. 2. Portions of the housing structure are made of transparent plastic material to permit light to pass between the light source D1 and the first light sensitive component D3.

Figure 3:
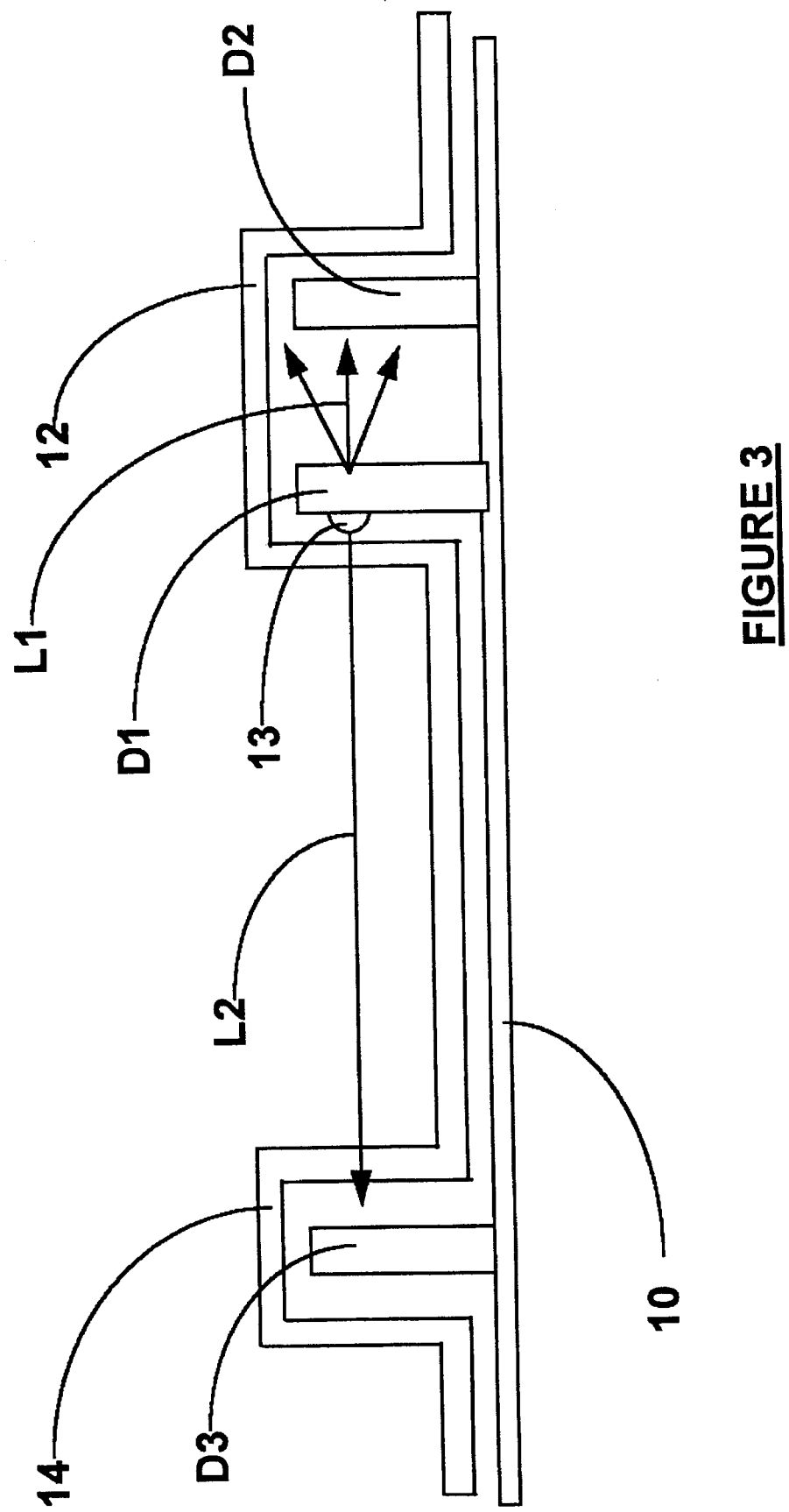
FIG. 3 illustrates the components of FIG. 2 attached together.

FIG. 3 illustrates the platform 10 associated with the housing structure to place the light source D1 and the second light sensitive component D2 within the first compartment 12 and the first light sensitive component D3 within the second compartment 14. When arranged in this manner, light from the light source D1 can pass through transparent walls of the first and second compartments and be received by the first light sensitive component D3. The area between the first and second compartments, 12 and 14, is shaped to permit a fluid to pass through the region between the compartments. In this manner, the turbidity of the fluid located between the first and second compartments can be measured by monitoring the intensity of the light received by the first light sensitive component D3. As illustrated in FIG. 3, the present invention places the second light sensitive component D2 within the same housing compartment 12 with the light source D1. Many different types of light emitting diodes emit light in all directions. Therefore, the light emitted in the direction represented by arrow L1 can be received by the second light sensitive component D2. In this manner, the second light sensitive component D2 can be used to monitor the intensity of light provided by the light source D1. If, for any reason, the intensity of light being emitted by the light source D1 is not equivalent to a predetermined magnitude, steps can be taken by an associated control circuit to increase the current provided to the light source D1 in order to increase the intensity of light emitted therefrom. Similarly, if the amount of light emitted from the light source D1 is greater than a predetermined threshold, the current provided to the light source D1 can be decreased. Since no fluid passes between the light source D1 and the second light sensitive component D2, the amount of light received by the second light sensitive component D2 will be unaffected by external factors and can be used for the purpose of controlling the light emitted by the light source. Since the present invention permits the light source D1 to be controlled so that a constant light intensity is emitted from it, the light magnitude received by the first light sensitive component D3 will be an accurate and reliable indication of the turbidity between the compartments, 12 and 14.

In FIGS. 2 and 3, the light emitting diode D1 is shown as having a lens 13 which focuses the light that is transmitted in the direction of the first light sensitive component D3. This results in a focused light beam L2. The light emanating from the light emitting diode D1 in the opposite direction toward the second light sensitive component D2 is unfocused. This light is identified as L1 in FIGS. 2 and 3.

Figure 4:
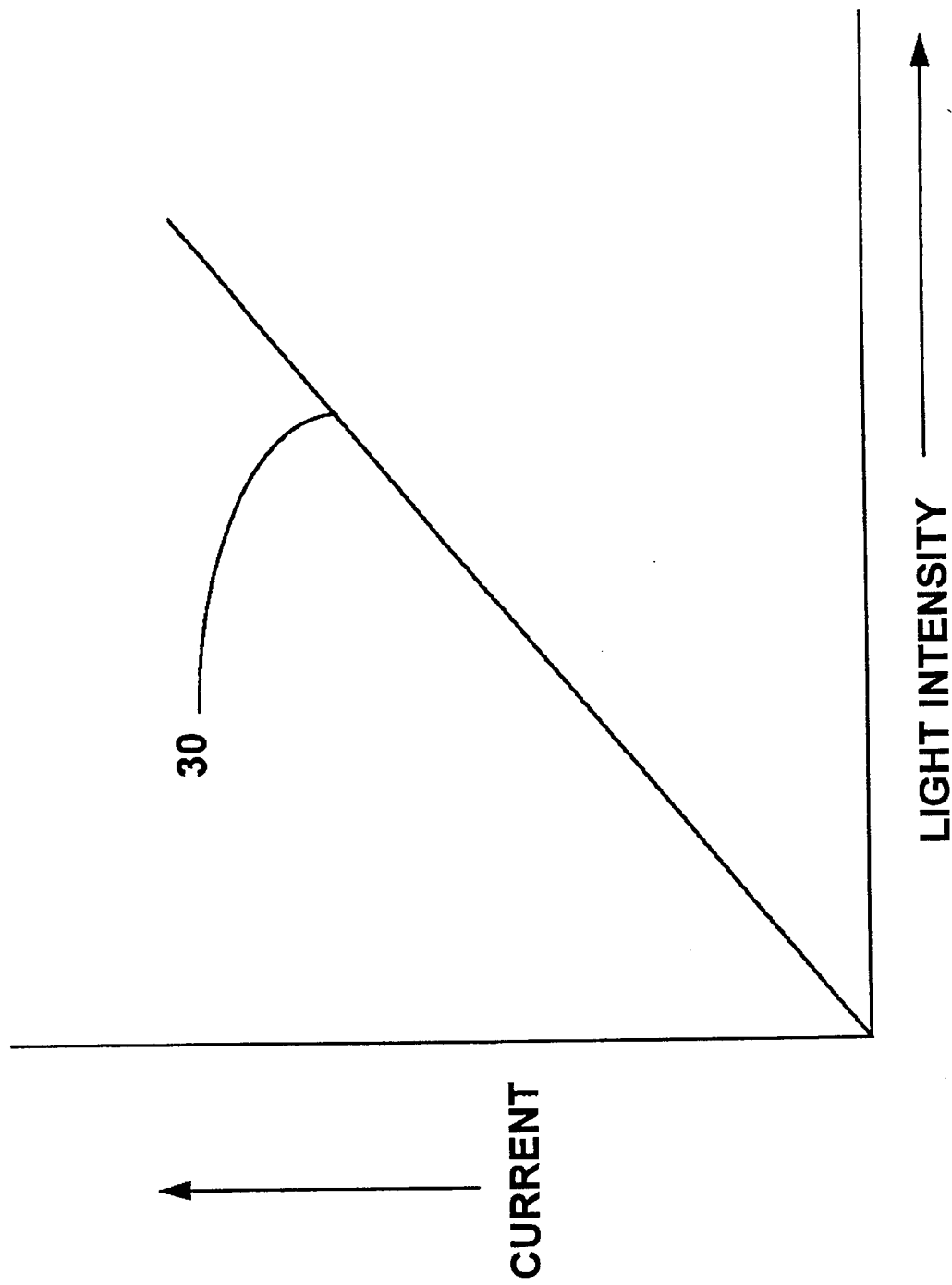
FIG. 4 is a graphical representation of the relationship between the current signal provided by a photodiode and the light intensity on the photodiode.

The signal provided by a light sensitive component, such as a photodiode, is generally linear with respect to the light intensity imposed on the diode. This is represented in FIG. 4 to show that the current flowing through a photodiode is generally linear with respect to the light intensity on the diode. Therefore, the signal provided by a photodiode is a reliable means for determining the actual intensity of light being received by the diode.

Figure 5:
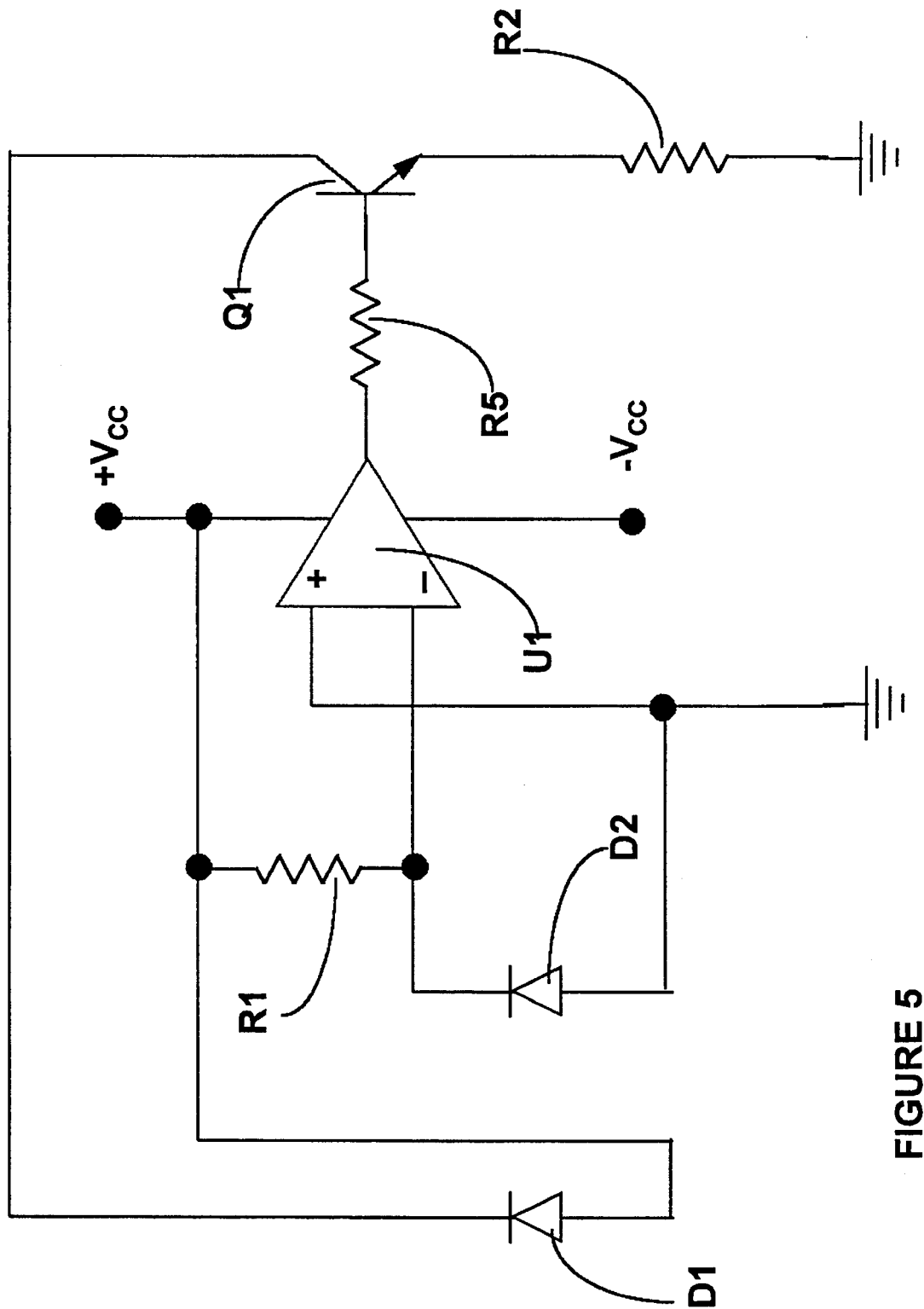
FIG. 5 illustrates an exemplary electronic circuit that can be used in conjunction with the present invention.

FIG. 5 illustrates a circuit that can be used in conjunction with the present invention to regulate the light intensity emitted by the light source D1. Light emitted by the light source D1 is received by the second light sensitive component D2. The current flowing through the second light sensitive component D2, which is illustrated as a photodiode, is received by the inverting input of the FET input operational amplifier U1. The FET input operational amplifier helps to avoid input current that would disadvantageously add to the photo diode current and represent an error. Either JFET input operational amplifiers or CMOS operational amplifiers can be used for these purposes. The difference between the signal at the inverting input of the operational amplifier and the ground potential which is connected to the noninverting input of the operational amplifier is represented by the output of the operational amplifier. This output is connected to the base of transistor Q1. Therefore, the intensity of the output from the operational amplifier U1 controls the current flowing through transistor Q1. This, in turn, controls the current flowing through the light source D1 which, in this case, is a light emitting diode. The circuit shown in FIG. 5 is only one example of how the configuration of the present invention can be used to control the light intensity from the light source D1.

With continued reference to FIG. 5, operational amplifier U1 is a field effect transistor input operational amplifier. Resistor R1 is selected to set the desired detector current which can be approximately 150 microamperes. Resistor R2 and the input voltage $V_{CC}$ determine the maximum LED current which can be approximately 30 milliamperes. As described above, the second light sensitive component D2 is a photodiode which is disposed at the back side of the light emitting diode D1. In a preferred embodiment of the present invention, the light source D1 is a tight beam sidelooker LED such as that which is identified by Catalog Number SEP8736 which is available in commercial quantities from the MICRO SWITCH division of Honeywell. The operational amplifier U1 can be Catalog Number LF351 which is available in commercial quantities from Texas Instruments. The first and second light sensitive components, D2 and D3, can be photodiodes such as Catalog Number VTB100 which is available in commercial quantities from EG&G.

Figure 6:
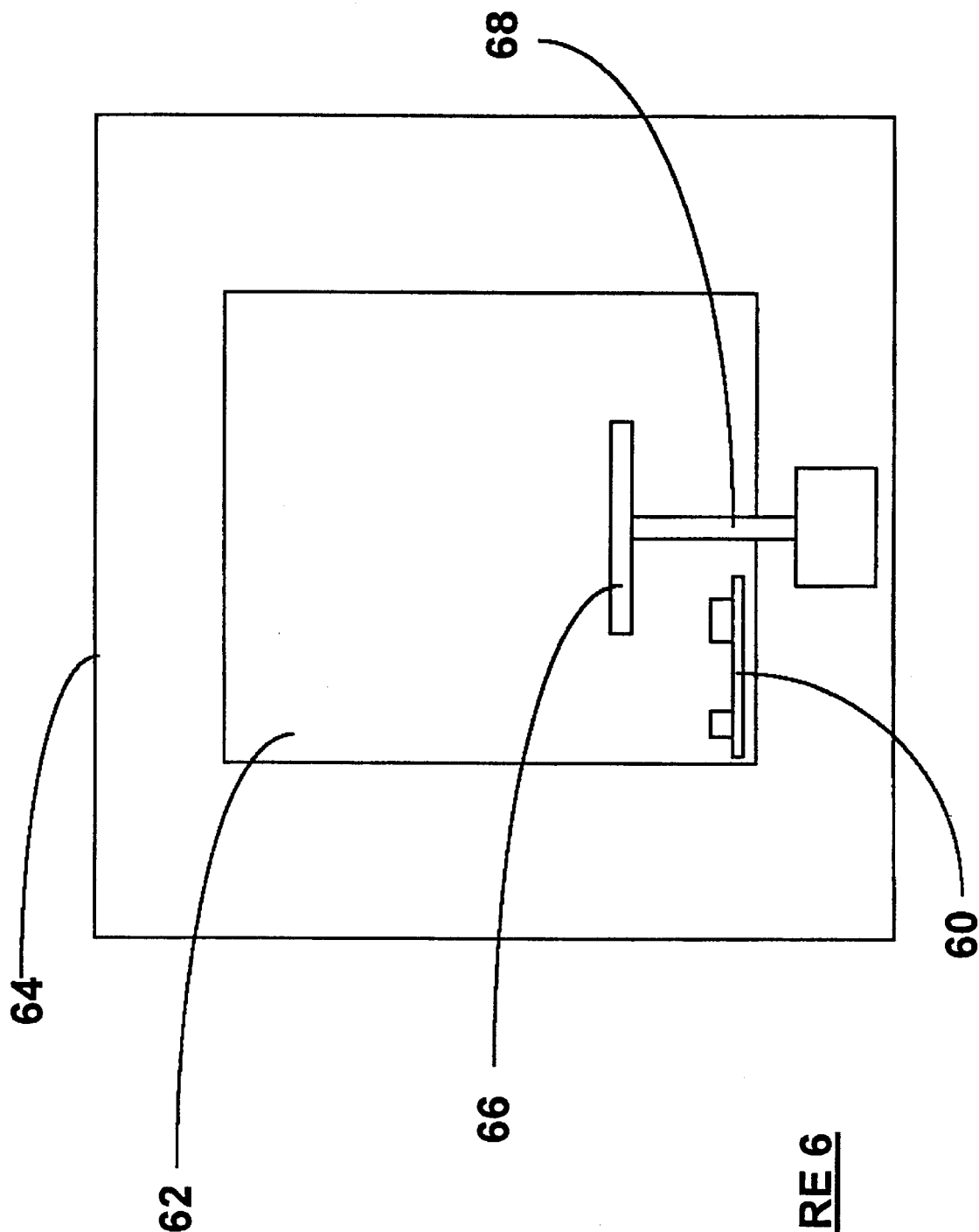
FIG. 6 is a schematic representation of a machine for washing articles in association with a turbidity sensor.

FIG. 6 illustrates one exemplary application of a turbidity sensor made in accordance with the present invention. The turbidity sensor, which is identified by reference numeral 60 in FIG. 6, is disposed near the bottom portion of a fluid containment 62 within a dishwasher 64. A wash arm 66 is rotated about a shaft 68. When the containment 62 is partially filled with water, the turbidity sensor 60 is submerged. Movement of water over the turbidity sensor 60, in the region between the first and second compartments, allows the turbidity sensor to measure the turbidity of the fluid and thereby allows the dishwasher to control its operation in an efficient manner. It should be understood that the illustration in FIG. 6 is highly schematic and simplified for the purpose of clarity.

As described above, a preferred embodiment of the present invention provides a solid state optoelectronic turbidity sensor which uses only the transmitted optical beam for measuring turbidity, but uses a second light sensitive component to directly sense a fixed fraction of the light output from an LED. The use of these two photodetectors makes it possible to eliminate the effects of changes in the LED as a function of both time and temperature. The turbidity sensor is intended for use in appliances, such as dishwashers and clothes washers, to sense the cleanliness of the water within the appliance. The optoelectronic components are an LED and two photodiode detectors that are supported by a platform such as a printed circuit board. The first light sensitive component is mounted on the optical axis of the LED so that light from the LED must pass through the possibly turbid solution in order to reach the first light sensitive component. Because of this physical arrangement, the optical signal received by the first light sensitive component is a monotonic function of the turbidity of the solution. The second light sensitive component is mounted near the LED so that it intercepts a constant fraction of the light from the LED. The second light sensitive component responds only to the LED output and is not affected by the turbidity of the solution. The component configuration illustrated in the Figures and described above is provided for purposes of describing the present invention and does not limit its scope. The LED and the photodiodes used in a particularly preferred embodiment of the present invention are in sidelooker packages. If, on the other hand, an axial lead package is used for the LED, the leads would be bent so that the optical axis remains substantially parallel to the surface of the printed circuit board. The second light sensitive element does not have to be a separate component. Since its primary role is to monitor a fixed fraction of the light output of the LED, the second light sensitive element can be a photodiode chip included in the same plastic package with the LED to form a combined component with the LED and photodiode contained therein. This type of combined component requires at least three leads to provide electrical access to both the LED chip and photodiode chip. Throughout the Description of the Preferred Embodiment, the light receiving devices are described as the first and second light sensitive components. However, it should be understood that this terminology does not restrict the present invention to the use of individual components. Instead, this terminology includes within its scope the implementation of the present invention with the LED and second photodiode being implemented as elements of a common package. In other words, in the terminology of the Description of the Preferred Embodiment of the present invention, the second light sensitive component can be an element or chip within a common package that also contained the LED. The housing is a transparent barrier that is used to isolate the components on the printed circuit board from the turbid solution. The use of this housing greatly enhances the reliability of the electronic assembly and also benefits the optical performance of the device. Since the molded lens on the LED package is surrounded by air, it maintains its full optical focusing ability. If, on the other hand, the LED lens was surrounded by water, much of the focusing ability of the lens would be lost due to the index of refraction of the water. In the configuration illustrated in the Figures, the lens on the LED can be selected to maximize the power that reaches the first light sensitive component when the solution is clear and the turbidity is very low. By selecting the beam angle of the LED, the coupled power can be selected as a design tradeoff against the ease of assembly and alignment of the components. The improved coupling between the LED and the first light sensitive component can be used in several ways to achieve a robust turbidity sensor. Increased current of the first light sensitive component will make it possible to use a smaller feedback resistor in that circuit. This will improve the reliability of the electronic assembly in the harsh environment encountered in most appliances. With better optical coupling, the LED drive current can be reduced. This will improve the life of the LED component and reduce power dissipation in the electronic assembly. The two compartments illustrated in the Figures is similar to other turbidity sensors that are known to those skilled in the art. When the present invention is used, the first compartment contains both an LED and the second light sensitive component. In existing turbidity sensors, the first compartment contains only a light source. The arrangement of the two compartments serves to block stray light that is emitted from all surfaces of a molded plastic LED package so that the stray light does not interfere with the proper functioning of the turbidity sensor. In the present invention, a portion of the stray light from the LED is used to monitor the LED output so that the turbidity measurement can be calibrated to the ratio of the response of the first and second light sensitive components. If an axial lead LED package is used, the second light sensitive component should be mounted at the side of the LED for best results rather than the LED as shown in the illustrations described above.

Photodiodes are predictably linear components. The output current is typically a linear function over at least nine decades of optical output and the temperature coefficient of response is quite low. The responsivity is constant over operating life and tracking between randomly picked photodiodes of the same type is highly reliable. On the other hand, light emitting diodes are notorious for their nonlinearity, a large temperature coefficient of light output versus current and degradation of light output with time of operation. The intensity of light output is predictable for light emitting diodes of the same type. However, the degradation rate for light emitting diodes of the same type can vary by a factor of 100 to 1 or more and, as they degrade, the temperature coefficient of light also output changes. The light emitting diode is not recognized as a stable and reliable analog signal source and should not be used in that mode.

The primary purpose of the present invention is to provide a means for measuring turbidity that is substantially independent of the undesirable and unpredictable characteristics of light emitting diodes. This is accomplished by monitoring the LED output with the second light sensitive component while measuring a signal related to the turbidity of the solution with the first light sensitive component. The temperature and age induced variations of the LED output can be removed from the turbidity sensor response by relating the turbidity to the ratio of the two photodiode signals. Two modes of operation can be used in a turbidity sensor made in accordance with the present invention. The signal from the second photodiode can be used in a feedback loop to adjust the LED drive current in such a way that the optical output of the LED is rendered independent of both time and temperature. In this case, the signal from the first photodiode is used as a direct monotonic measure of the turbidity with the signal decreasing in response to increasing turbidity. The optical feedback can be either analog or digital. This is similar to the optical feedback used on most laser diodes to stabilize their optical output. This technique has the disadvantage of changing the power dissipation, and therefore the temperature rise, in the electronic assembly as the LED characteristic changes. The LED can also be run at a constant current and the ratio of the response of the two photodiodes can be computed to obtain a monotonic measure of the turbidity. This technique has the advantage of constant power dissipation, and therefore temperature rise, in the electronic assembly. However, the degradation of the light output of the LED will cause a loss of signal-to-noise ratio in both photodiode channels that will lead to a loss in accuracy of the turbidity measurement.

When the water solution within the machine for washing articles is clean, the response of the first photodiode is maximum. As the turbidity of the solution increases, the response of the first photodiode decreases as light is scattered out of the beam by the soil in the solution. For low values of turbidity, very little light is scattered out of the beam and the change in the response ratio is small. Over the life of the appliance, it is probable that the response of the first light sensitive component in a clean solution will change due to build up of deposits on the shell surfaces that lie in the optical path. This build up of deposits can cause errors in measurement for low values of turbidity. The gradual build up of this type of error can be eliminated by reading and storing the response ratio between the signals from the two photodiodes at a time when the solution is known to be clean. This could be accomplished during the last clean water rinse in each cycle with that value being stored for use in the following cycle.

The combination of using the ratio of two photodiode signals in order to eliminate the variability of the LED light intensity and the reading and storing of the response ratio when the solution is known to be clean to eliminate slow changes in the optical path results in a robust and reliable turbidity sensor for use in appliances. Using a lensed LED surrounded by air greatly enhances the optical coupling between the LED and the first light sensitive component. This increase in optical coupling can be used to improve the manufacturability and reliability of the turbidity sensor made in accordance with the present invention. The two chambered aperture box minimizes unwanted wide angle light and helps provide a robust and reproducible turbidity sensor. The particular type of aperture box used in conjunction with the turbidity sensor is not limiting to the scope or operation of the present invention. One possible aperture arrangement that can be used is described in U.S. Pat. No. 3,485,013 which was filed on Jun. 16, 1994 by Cummins and assigned to the Assignee of the present application. The present invention can be used with aperture arrangements of this type or any other type that is suitable for use with turbidity sensors.

Figure 7:
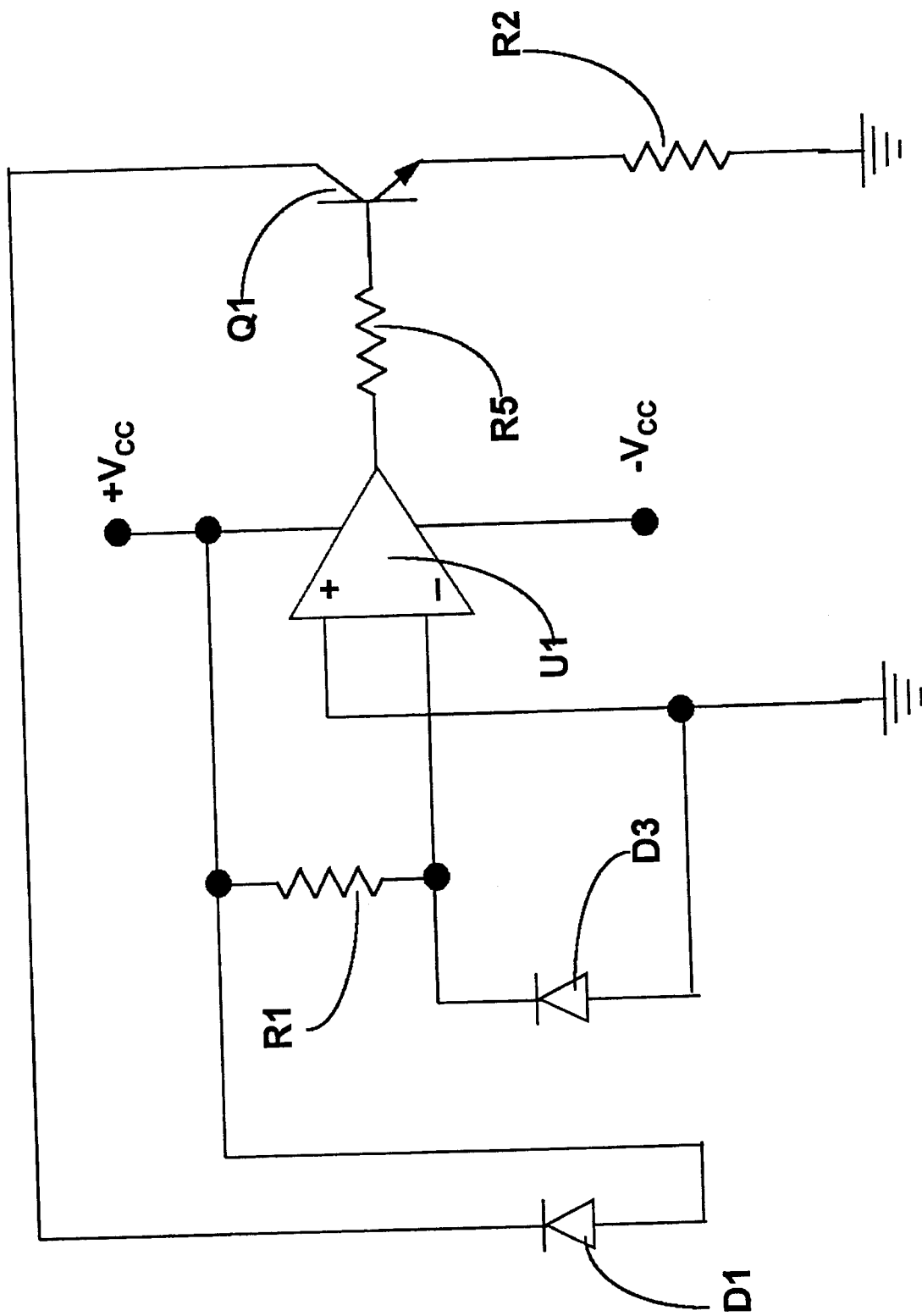
FIG. 7 illustrates an exemplary electronic circuit that can be used in conjunction with the present invention, wherein diode D2 of FIG. 5 has been replaced by diode D3.

The embodiment of the present invention described above in conjunction with FIG. 5 utilizes the second light sensitive component D2 in the feedback loop of operational amplifier U1. In this manner, the current passing through the light emitting diode D1 can be controlled so that the light received by the second light emitting diode D2, which is within the housing 12 and behind the light emitting diode D1, is maintained at a constant magnitude. The reasons for this procedure have been described in detail above in conjunction with FIG. 5. However, it should be understood that an alternative embodiment of the present invention can be achieved through a slight modification of the circuit shown in FIG. 5. Rather than using the second light sensitive component D2 in the feedback loop of the operational amplifier U1, the circuit shown in FIG. 5 could be modified to use the first light sensitive component D3 in the feedback loop of the operational amplifier. This alternative embodiment of the present invention is illustrated in FIG. 7. Operationally, the circuits shown in FIGS. 5 and 7 differ in the fact that they control the current flowing through the light emitting diode D1 as a function of two different light sensitive components. The embodiment illustrated in FIG. 7 uses the operational amplifier U1 to maintain the light intensity received by the first light sensitive component D3 at a constant level. In other words, as the turbidity of the fluid which is located within the space between the light emitting diode D1 and the first light sensitive component D3 increases in magnitude and the light transmitted along arrow L2 is more effectively blocked by the existence of particulates within this region, the operational amplifier U1 increases the current flowing through the light emitting diode D1 to raise the magnitude of light emanating from it. The current flowing through the light emitting diode D1 is continually increased as the turbidity of the monitored solution increases. In theory, the operation of this second embodiment of the present invention is significantly different from the operation of the first embodiment and this difference is achieved by the relatively minor alteration to the circuit shown in FIG. 5 as illustrated in FIG. 7. If the light received by the first light sensitive component D3 is held at a constant magnitude by the operational amplifier U1, the light received by the second light sensitive component D2 can be used to monitor the turbidity of the solution flowing in the region between the light emitting diode and the first light sensitive component. Because of the fact that the current flowing through the light emitting diode D1 increases as a function of the turbidity of the fluid, the light received by the second light sensitive component D2 also increases because of its position proximate the light emitting diode and the fact that no interference can occur with the light passing from the light emitting diode to the second light sensitive component, which is identified as L1 in FIG. 3.

Figure 8:
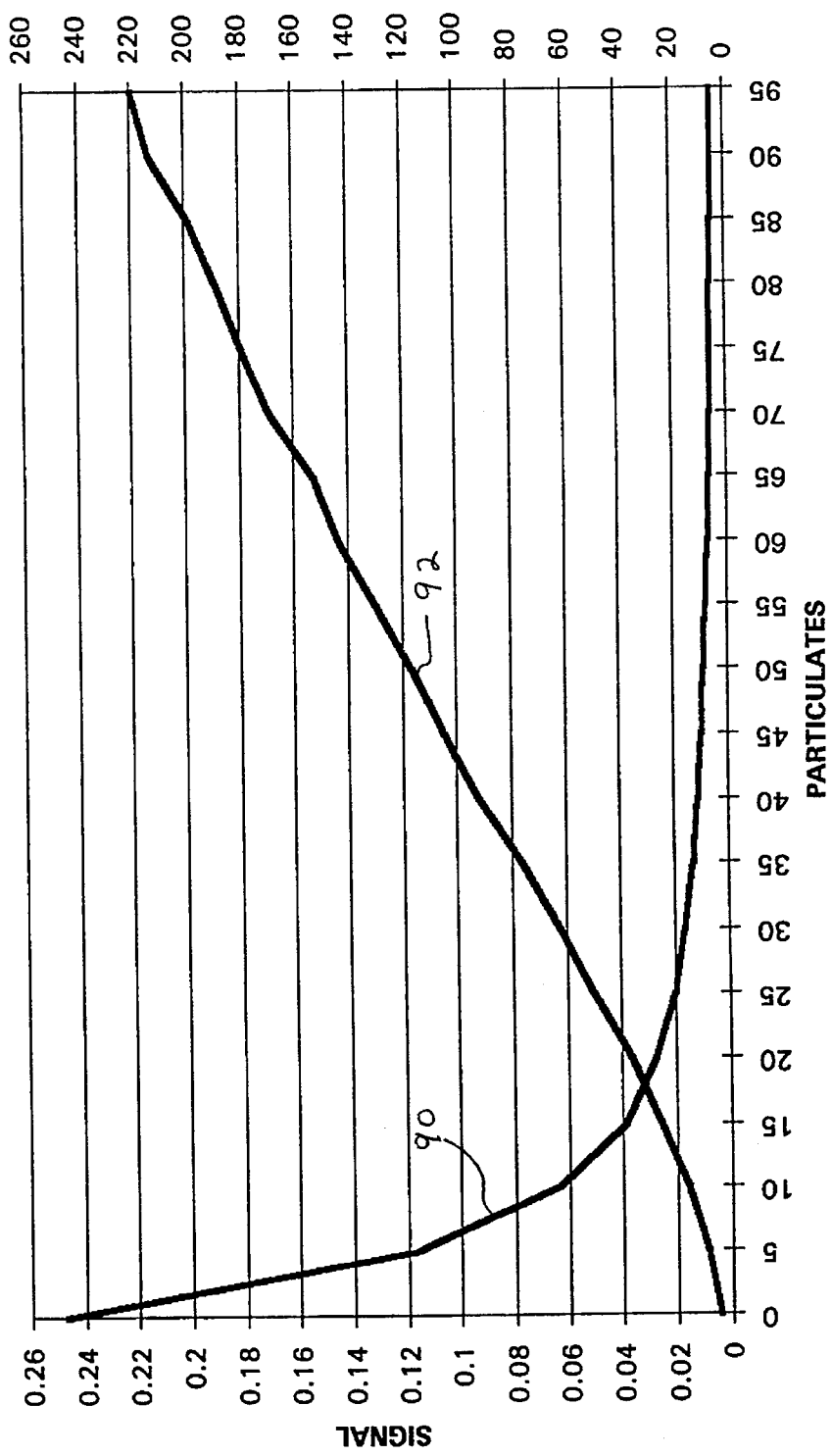
FIG. 8 shows a graphical representation of the signals provided by the first and second light sensitive components of the present invention.

FIG. 8 is a graphical representation that illustrates the change in signal level provided by the first and second light sensitive components, D3 and D3, as a function of the amount of particulates in the fluid being monitored. The results shown in FIG. 8 are the empirical results of tests performed with a prototype arrangement of the light emitting diode D1 in combination with the first and second light sensitive components, D3 and D2. The amount of particulates, as illustrated by the horizontal axis in FIG. 8, was controlled by adding droplets of milk to a water solution. The horizontal axis in FIG. 8 shows the number of droplets of 2% milk added to 24 cubic centimeters of tap water.

The results represented by line 90 in FIG. 8 show the change in the signal provided by the first light sensitive component D3 in response to increasing turbidity and the current flowing through the light emitting diode D1 being controlled to provide a constant magnitude of light received by the second light sensitive component D2. In other words, the left vertical axis in FIG. 8 represents the ratio of the signal received from the first light sensitive component D3 divided by the signal received by the second light sensitive component D2. As described above, in this first embodiment of the present invention, the light received by the second light sensitive component D2 is held to a constant magnitude. Therefore, increased turbidity will decrease the signal received by the first light sensitive component D3 and will also decrease the ratio represented by the left vertical axis in FIG. 8. As can be seen, the signal represented by line 90 can be used to represent the turbidity of the fluid being monitored. However, line 90 is highly nonlinear. The information provided by line 90 is highly sensitive in the range of turbidity less than 15, but much less sensitive in the higher ranges of turbidity.

With continued reference to FIG. 8, line 92 represents the information that is made available by the second embodiment of the present invention. In other words, line 92 represents the ratio of the signal received from the second light sensitive component D2 divided by the signal received from the first light sensitive component D3. Since the signal received from the first light sensitive component D3 is maintained at a constant magnitude as the magnitude of turbidity changes, the ratio of these signals increases as a function of turbidity. As described above, this relationship results from the fact that increased turbidity in the fluid being monitored causes the operational amplifier U1 to increase the current flowing through the light emitting diode D1. This increase in current through the light emitting diode D1, in turn, increases the light intensity received by the second light sensitive component D2. As can be seen in FIG. 8, the signal represented by line 92 is highly linear and has a relatively constant slope over a wide range of turbidity magnitudes. This linearity is advantageous in many turbidity measuring applications.

Although the present invention has been described in considerable detail and specifically illustrated to disclose a preferred embodiment, it should be known that alternative embodiments are also within its scope.

The embodiments of the invention in which an exclusive property or right is claimed are defined as follows:

1. A turbidity sensor, comprising:

a light source;

a first light sensitive component, said light source and said first light sensitive component being spaced apart to provide a gap therebetween, said gap being shaped to permit a fluid to be disposed between said first light sensitive component and said light source, light from said light source being transmittable through said fluid for receipt by said first light sensitive component, the intensity of said light received by said first light sensitive component being indicative of the level of turbidity of said fluid;

a second light sensitive component, said second light sensitive component being disposed proximate said light source, said first and second light sensitive components being photodiodes;

means for preventing said fluid from interfering with the transmission of light from said light source to said second light sensitive component;

means for regulating the intensity of light received by a preselected one of said first and second light sensitive components from said light source to a predetermined magnitude, said regulating means comprising a means for regulating the intensity of light received by said first light sensitive component by controlling the magnitude of current flowing through said light source;

means for comparing a first signal from said first light sensitive component to a threshold magnitude; and means for providing a second signal which is representative of the difference between said first signal and said threshold magnitude; and means for controlling an electrical current provided to said light source as a function of said second signal.

2. The turbidity sensor of claim 1, wherein:

said second light sensitive component and said light source are individual elements in a common component package.

3. The turbidity sensor of claim 1, further comprising:

a machine for washing articles, said turbidity sensor being disposed within a water reservoir of said machine.

4. The turbidity sensor of claim 3, wherein:

said machine is a dishwasher.

\* \* \* \* \*